US012751933B2

(12) United States Patent
Jung et al.

(10) Patent No.: US 12,751,933 B2
(45) Date of Patent: Oct. 6, 2026

(54) HONEYBEE ANTIDOTE COMPOSITION

(71) Applicant: Andong National University Industry-Academic Cooperation Foundation, Andong-si (KR)

(72) Inventors: Chul Eui Jung, Seoul (KR); Yong Rak Kang, Sancheong-gun (KR)

(73) Assignee: Andong National University Industry-Academic Cooperation Foundation, Andong-si (KR)

( * ) Notice: Subject to any disclaimer, the term of this patent is extended or adjusted under 35 U.S.C. 154(b) by 332 days.

(21) Appl. No.: 18/601,964

(22) Filed: Mar. 11, 2024

(65) Prior Publication Data

US 2025/0205177 A1 Jun. 26, 2025

(30) Foreign Application Priority Data

Dec. 21, 2023 (KR) ........................ 10-2023-0188157

(51) Int. Cl.
*A61K 31/12* (2006.01)
*A61P 39/02* (2006.01)

(52) U.S. Cl.
CPC .............. *A61K 31/12* (2013.01); *A61P 39/02* (2018.01)

(58) Field of Classification Search
CPC ................................ A61K 31/12; A61P 39/02
See application file for complete search history.

(56) References Cited

PUBLICATIONS

Rasmussen, Erik & Seier, Kristine & Pedersen, Ingrid & Kreibich, Claus & Amdam, Gro & Münch, Daniel & Dahl, John. (2021). Screening bioactive food compounds in honey bees suggests curcumin blocks alcohol-induced damage to longevity and DNA methylation. Scientific Reports. 11. 19156. 10.1038/s41598-021-98614-4.*

Strachecka, Aneta & Olszewski, Krzysztof & Paleolog, Jerzy. (2015). Curcumin Stimulates Biochemical Mechanisms of Apis Mellifera Resistance and Extends the Apian Life-Span. Journal of Apicultural Science. 59. 10.1515/JAS-2015-0014.*

"Density and Concentration Calculator for Mixtures of Ethanol and Water at 20° C.," handymath.com, Accessed Apr. 4, 2026, <https://www.handymath.com/cgi-bin/ethanolwater3.cgi?submit=Entry>.*

Hanine Almasri et al., "Physiological effects of the interaction between Nosema ceranae and sequential and overlapping exposure to glyphosate and difenoconazole in the honey bee *Apis mellifera*", Ecotoxicology and Environmental Safety, 2021, pp. 1-11, vol. 217, No. 112258.

Aneta J. Strachecka et al., "Curcumin Stimulates Biochemical Mechanisms of Apis Mellifera Resistance and Extends the Apian Life-Span", J. Apic. Sci., 2015, pp. 129-141, vol. 59, No. 1.

Erik M. K. Rasmussen et al., "Screening bioactive food compounds in honey bees suggests curcumin blocks alcohol-induces damage to longevity and DNA methylation", Scientific reports, 2021, vol. 11, No. 19156.

* cited by examiner

*Primary Examiner* — Alicia L Otton
(74) *Attorney, Agent, or Firm* — You & IP, LLC

(57) ABSTRACT

Proposed is a honeybee antidote composition for a carbaryl insecticide, the composition containing curcumin at a concentration in a range of 30 to 300 ppm, and a method of reducing toxic damage to a honeybee from a carbaryl insecticide. The method comprises preparing a 50% sucrose aqueous solution; adding curcumin to the prepared 50% sucrose aqueous solution to a concentration in a range of 30 to 300 ppm; and feeding a honeybee the 50% sucrose aqueous solution comprising curcumin.

2 Claims, 17 Drawing Sheets

HONEYBEE ANTIDOTE COMPOSITION

STATEMENT REGARDING GOVERNMENT SPONSORED RESEARCH

This invention was supported by the Rural development Administration. Research Subject name: "Development of the method for damage mitigation against pesticides and the investigation of colony collapse mechanism in honey bee"; Research Subject Number: PJ01577802.

CROSS REFERENCE TO RELATED APPLICATION

The present application claims priority to Korean Patent Application No. 10-2023-0188157, filed Dec. 21, 2023, the entire contents of which is incorporated herein for all purposes by this reference.

BACKGROUND OF THE DISCLOSURE

1. Field of the Disclosure

The present disclosure relates to a honeybee antidote composition and, more specifically, to a honeybee antidote composition provided as supplementary food to increase the survival rate of honeybees poisoned by a carbaryl insecticide.

2. Description of the Related Art

Honeybees are important insect pollinators. Severe damage to honeybees resulting from pesticide poisoning is increasing. In particular, the pesticide poisoning of honeybees in apple orchards in the spring is caused mainly by a chemical insecticide called carbaryl.

Carbaryl, a synthetic carbamate acetylcholinesterase inhibitor and suspected endocrine disruptor, is commonly used in agriculture for pest control due to having broad spectrum and low toxicity to mammals. The wide range of applications thereof extends to lawn and garden environments. However, the potential harm to Hymenoptera, especially honeybees, highlights environmental concerns. Despite being effective, the use of carbaryl has led to increased scrutiny of its impacts on ecosystems and emphasizes the need for responsible pest management practices and the exploration of alternative solutions.

Like all living organisms, honeybees have detoxification mechanisms by which toxic substances are neutralized and removed. Studies have shown that a group of enzymes such as P450, GST, and COE are involved in the detoxification of insecticides and secondary metabolites in honeybees. Typically, honeybees activate such detoxification mechanisms when exposed to toxic insecticides.

However, the ongoing exposure of honeybees to various insecticides and toxic substances remains a major cause of a decline in the honeybee population, which is problematic.

SUMMARY OF THE INVENTION

Therefore, the present disclosure aims to provide a honeybee antidote composition capable of serving as an effective antidote for insecticide toxicity to honeybees.

To achieve the objective described above, a honeybee antidote composition for a carbaryl insecticide, according to the present disclosure, contains curcumin at a concentration in a range of 30 to 300 ppm. Curcumin capable of increasing the survival rate of honeybees poisoned by a carbaryl insecticide while serving as an effective antidote for insecticide toxicity to honeybees may be provided at a concentration in a range of 30 to 300 ppm.

In this case, when curcumin has a concentration in the range of 90 to 110 ppm, curcumin may increase the survival rate of honeybees poisoned by the carbaryl insecticide and serve as an effective antidote for insecticide toxicity to honeybees. Therefore, curcumin is preferably provided at the most preferable concentration in the range of 90 to 110 ppm.

On the other hand, a method of reducing toxic damage to honeybees from a carbaryl insecticide includes the following steps: preparing a 50% sucrose aqueous solution; adding curcumin to the prepared 50% sucrose aqueous solution to a concentration in a range of 30 to 300 ppm; and feeding honeybees the 50% sucrose aqueous solution containing curcumin. This method enables curcumin capable of increasing the survival rate of honeybees poisoned by the carbaryl insecticide while serving as an effective antidote for insecticide toxicity to honeybees to be provided at a concentration in a range of 30 to 300 ppm.

Additionally, in the step of adding curcumin to a concentration in a range of 30 to 300 ppm, when the 50% sucrose aqueous solution contains curcumin at a concentration in the range of 90 to 110 ppm, curcumin may increase the survival rate of honeybees poisoned by the carbaryl insecticide and serve as an effective antidote for insecticide toxicity to honeybees. Therefore, curcumin is preferably provided at the most preferable concentration in the range of 90 to 110 ppm.

According to the present disclosure, curcumin is provided at the most preferable concentration in a range of 90 to 110 ppm. As a result, curcumin can increase the survival rate of honeybees poisoned by a carbaryl insecticide while serving as an effective antidote for insecticide toxicity to honeybees.

Additionally, curcumin can not only increase the survival rate of honeybees poisoned by the carbaryl insecticide but also perform a better role in the detoxification of honeybees from the insecticide toxicity and dramatically increase the activity of oxidases performing a role in detoxification.

DESCRIPTION OF THE PREFERRED EMBODIMENTS

Hereinafter, a honeybee antidote composition, according to a preferred embodiment of the present disclosure, will be described in detail with reference to the attached drawings.

Figure 1:
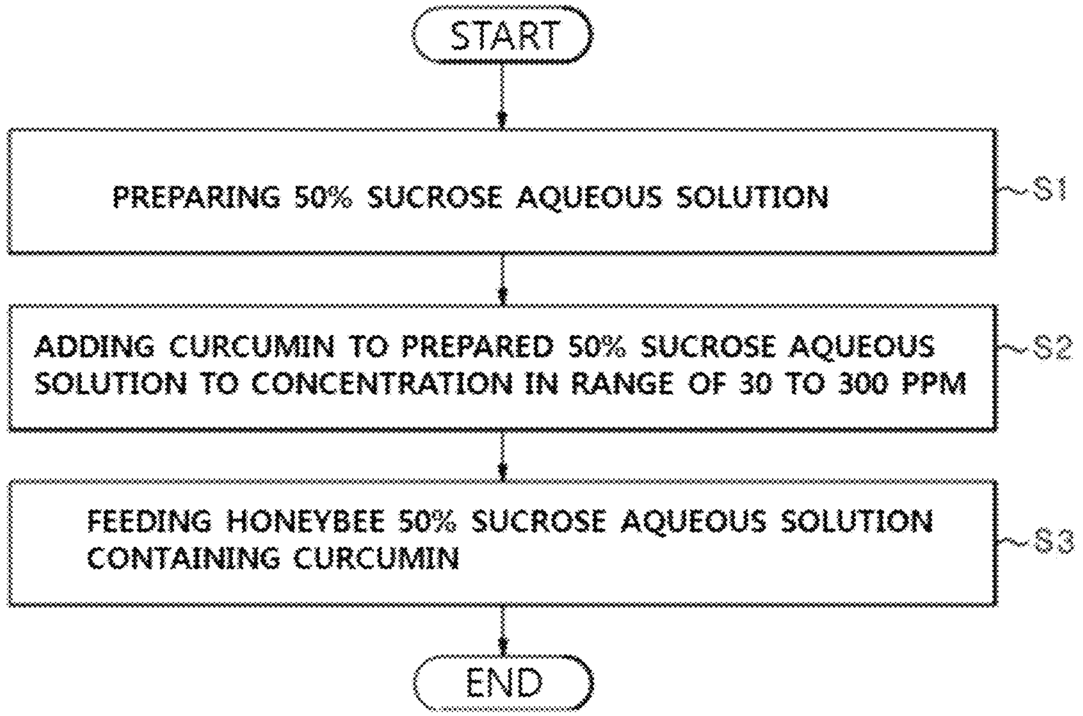
FIG. 1 is a flow chart showing a method of reducing toxic damage to honeybees from a carbaryl insecticide according to the present disclosure.
Figure 2:
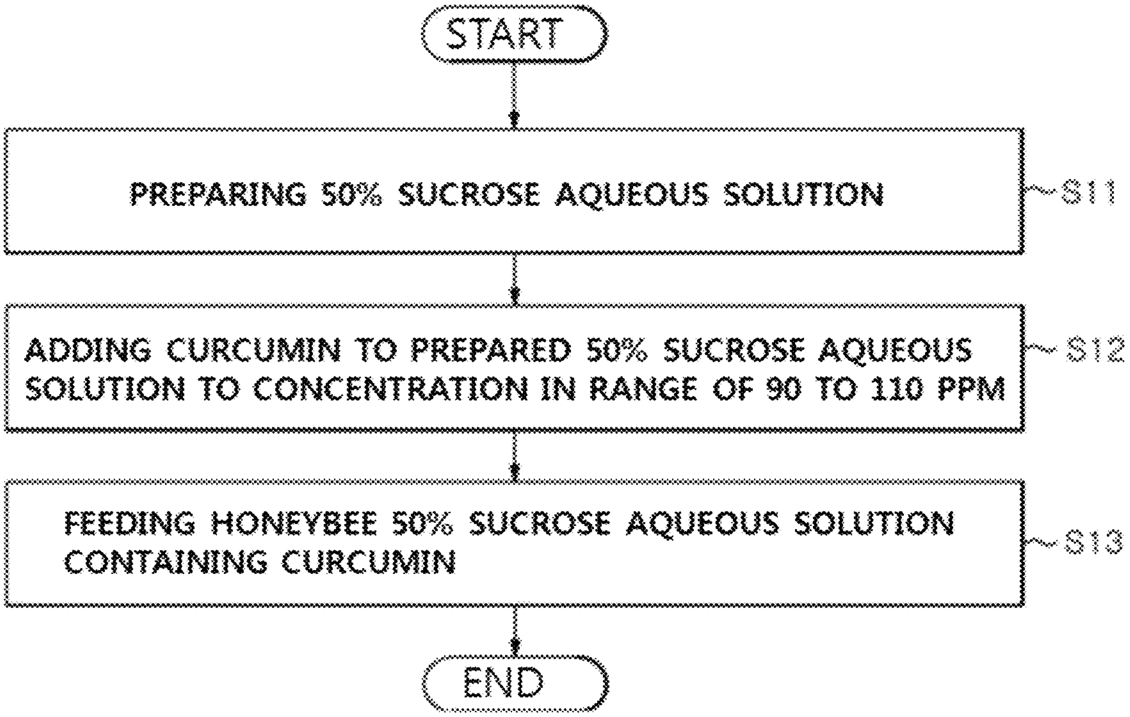
FIG. 2 is a flow chart showing a method of reducing toxic damage to different honeybees from a carbaryl insecticide.
Figure 3A:
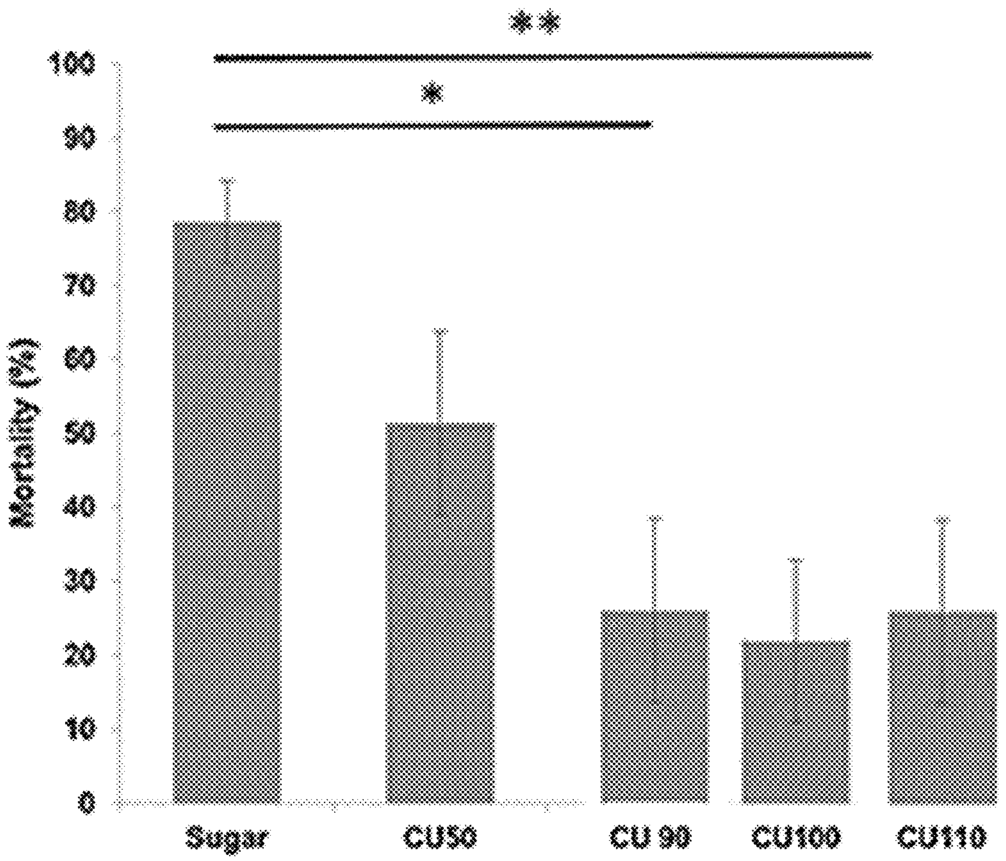
FIGS. 3A and 3B show graphs for explaining the impact of curcumin application at varying concentrations on the survival of honeybees and foragers (3B) topically poisoned by carbaryl.
Figure 3B:
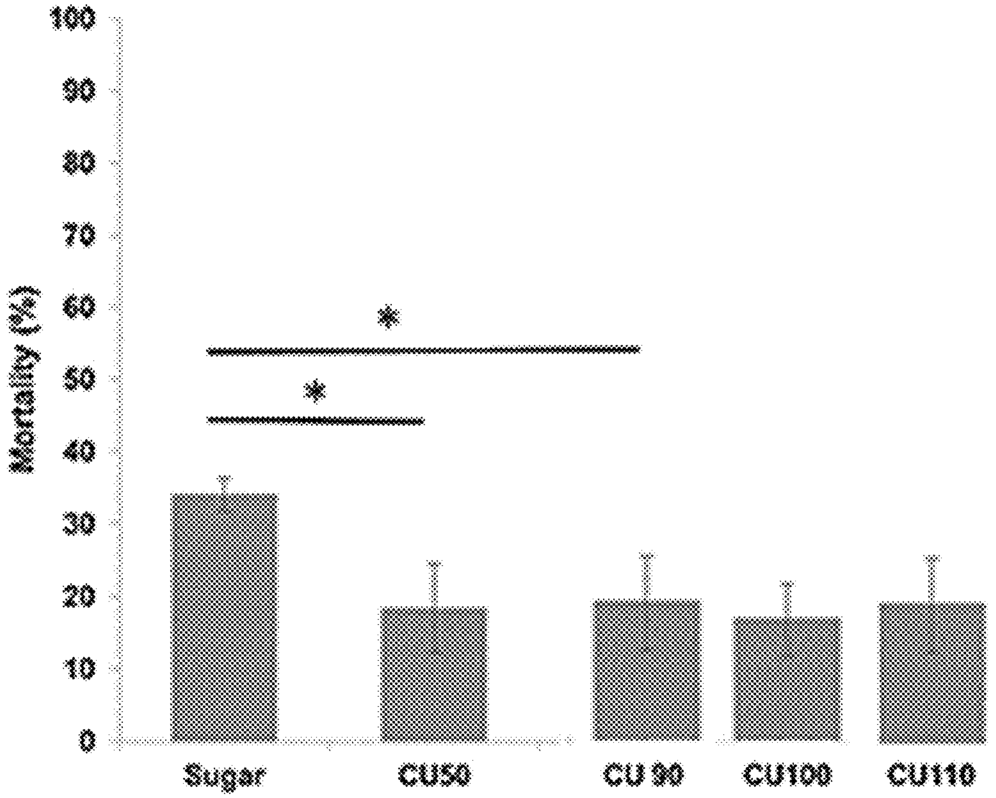
Figure 4:
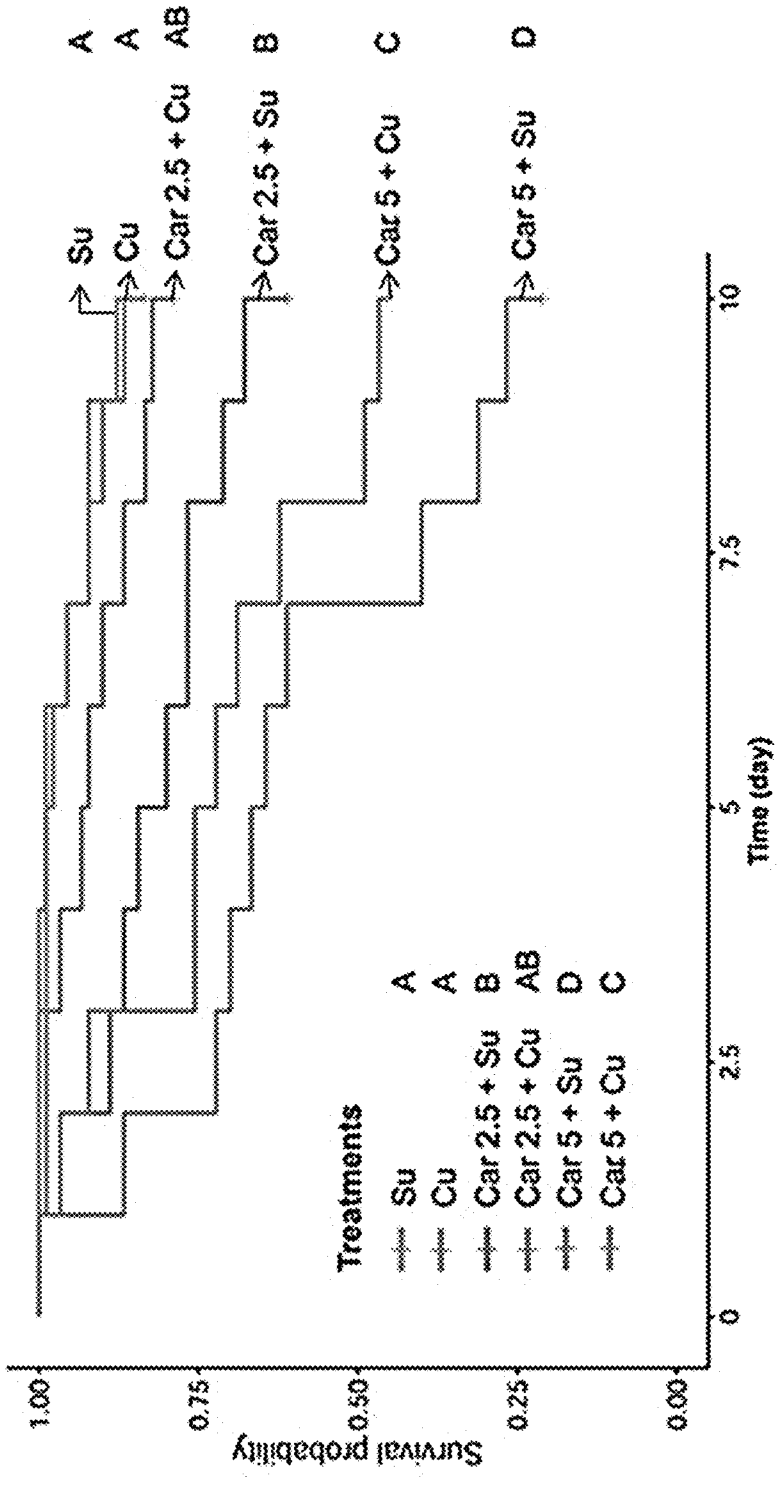
FIG. 4 is a graph of a Kaplan-Meier survival curve for test honeybees (*Apis mellifera*) chronically exposed to 2.5 and 5 ppm of carbaryl through oral exposure.
Figure 5A:
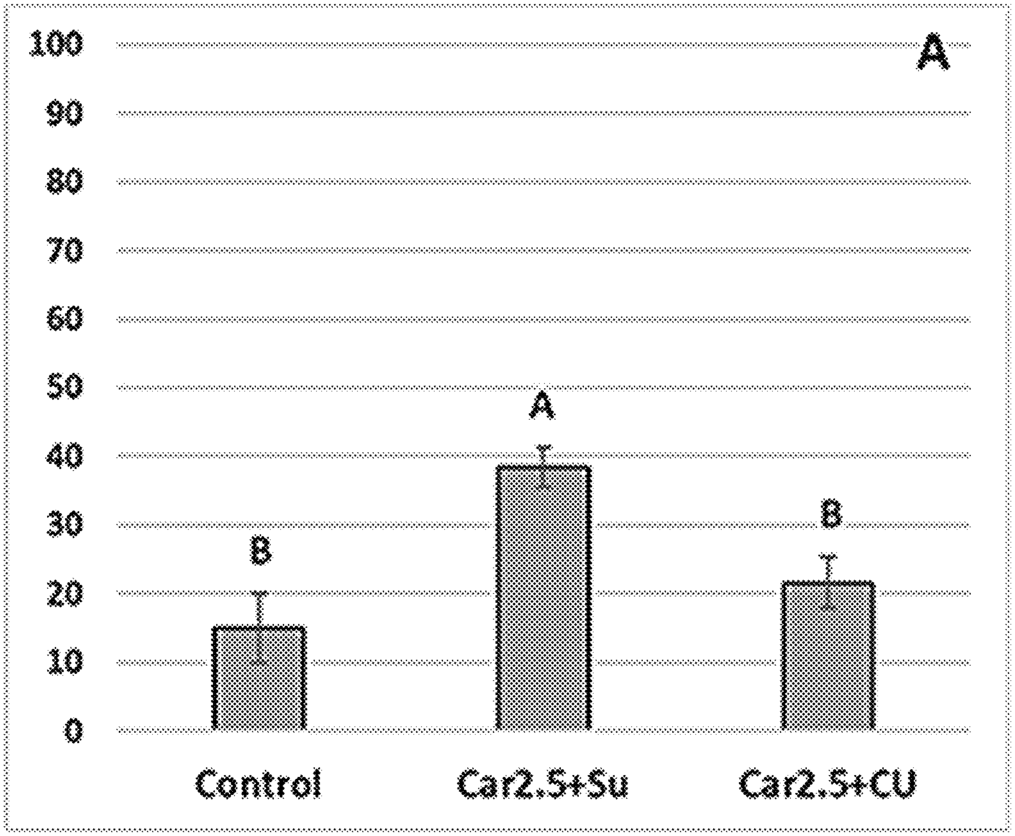
FIGS. 5A and 5B show graphs of the mortality rate of honeybees for 10 days after being chronically exposed to 2.5 ppm (5A) and 5 ppm (5B) of carbaryl.
Figure 5B:
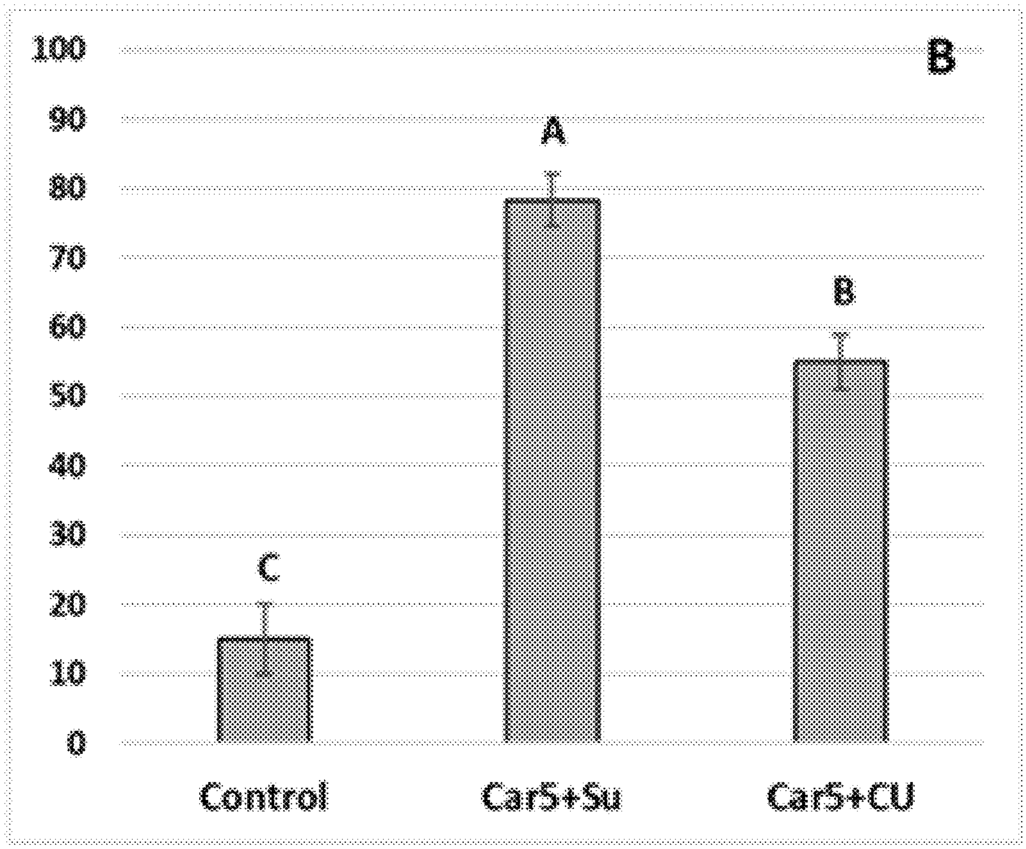
Figure 6A:
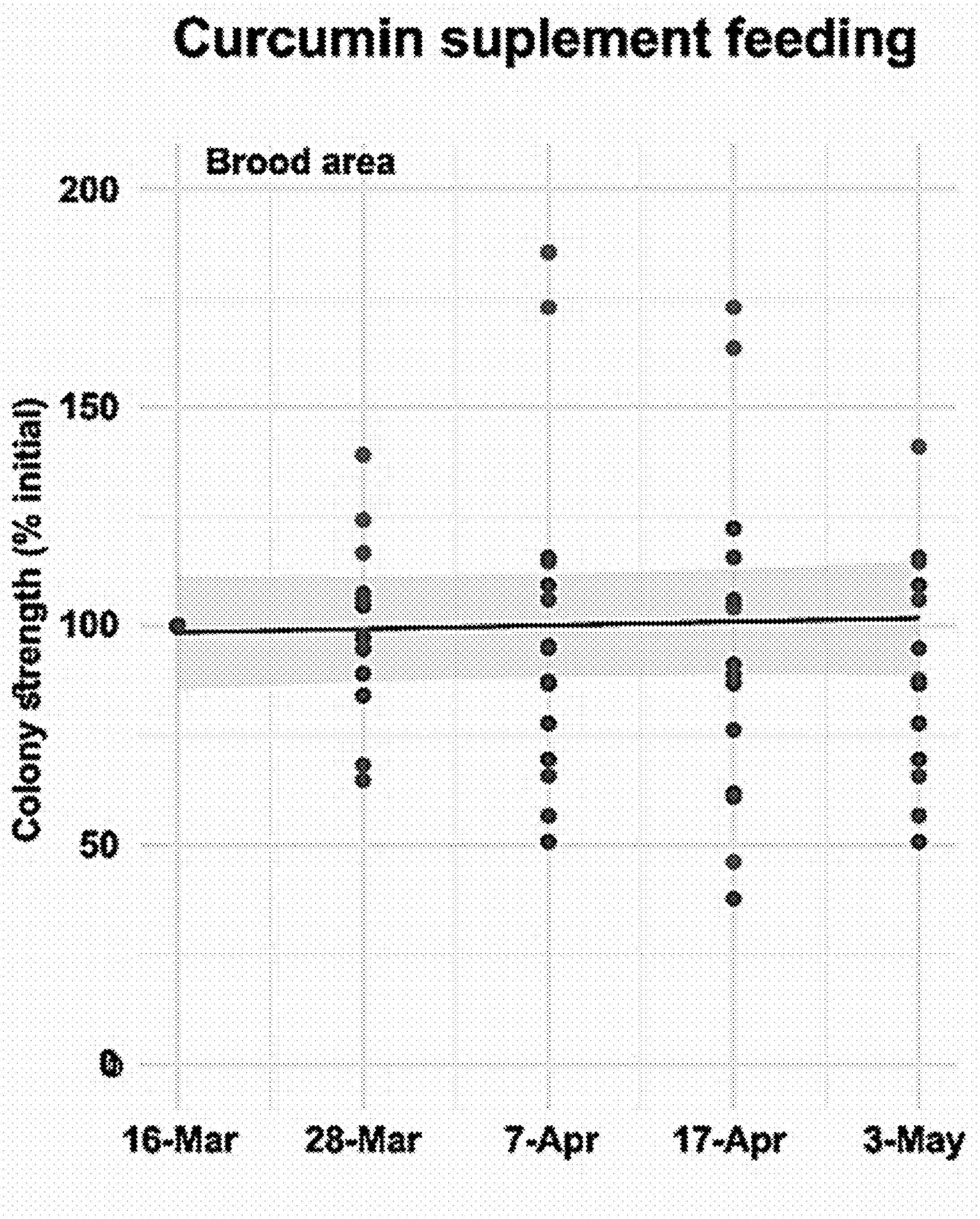
FIGS. 6A to 6D show graphs for explaining the impact of supplement application with 100 ppm of curcumin on the honeycomb area (6A to 6B) and the number of workers (6C to 6D) in hives given a solution supplemented with curcumin (100 ppm) (6A and 6C) and a common sugar solution (6B and 6D)
Figure 6B:
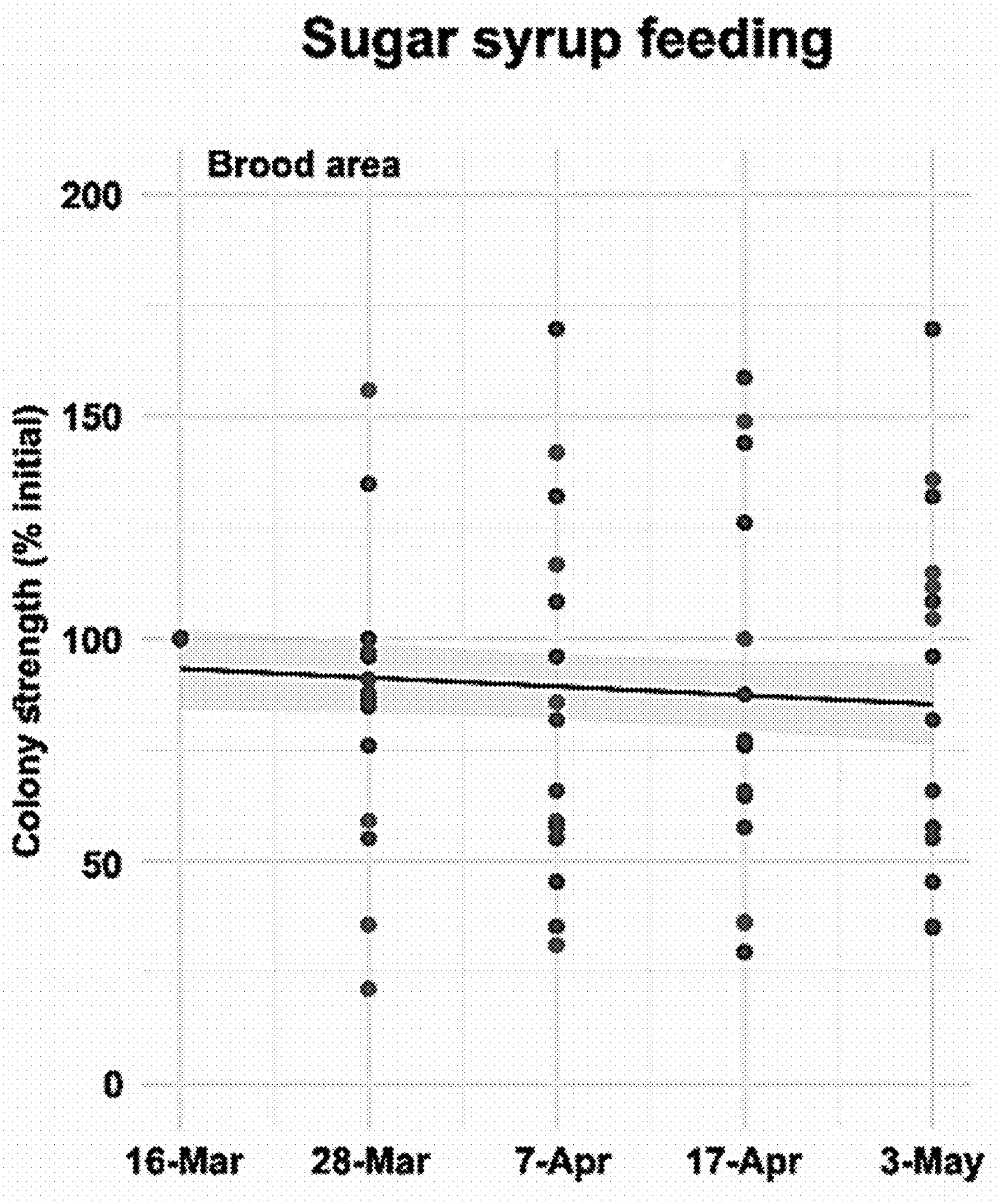
Figure 6C:
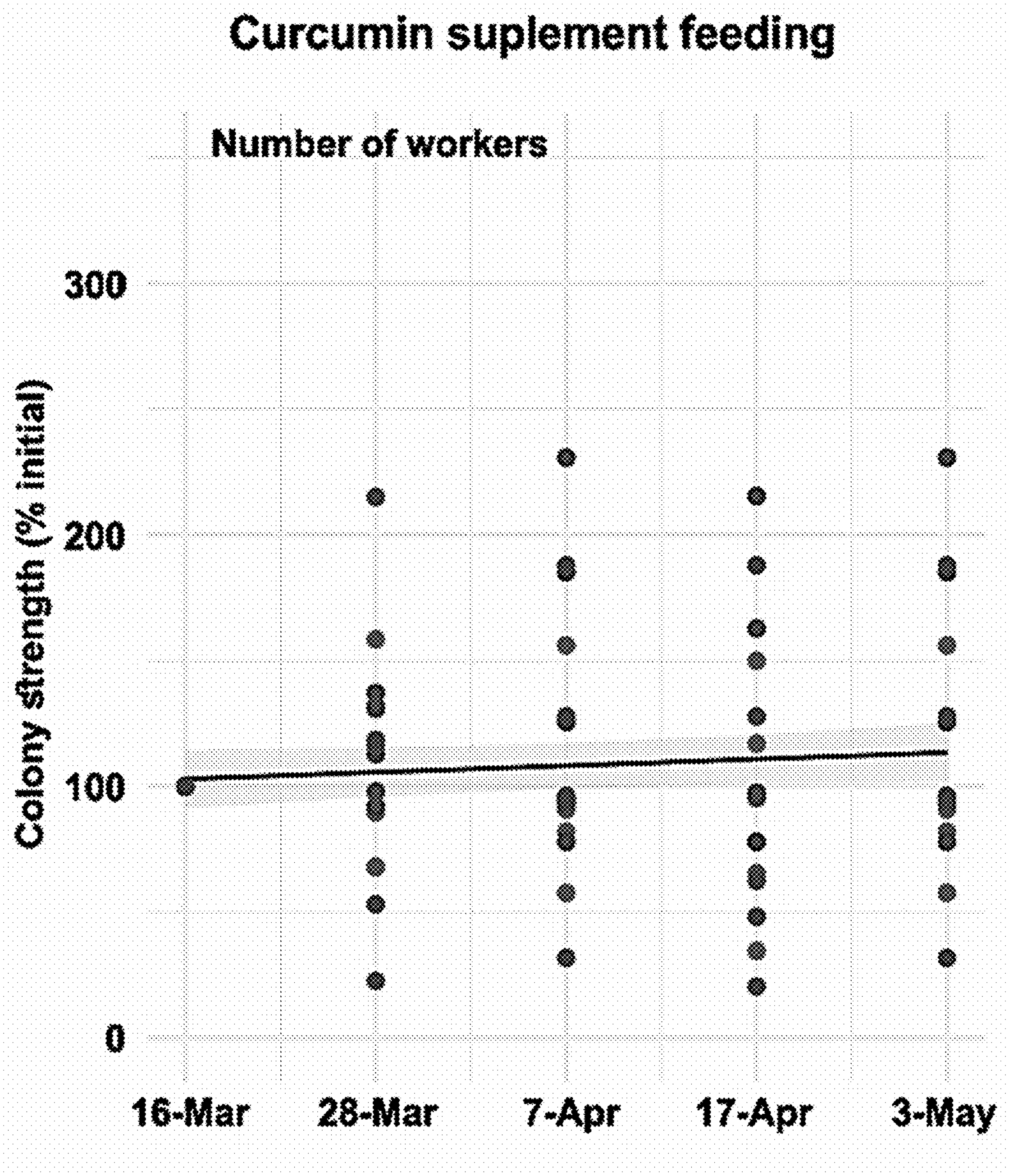
Figure 6D:
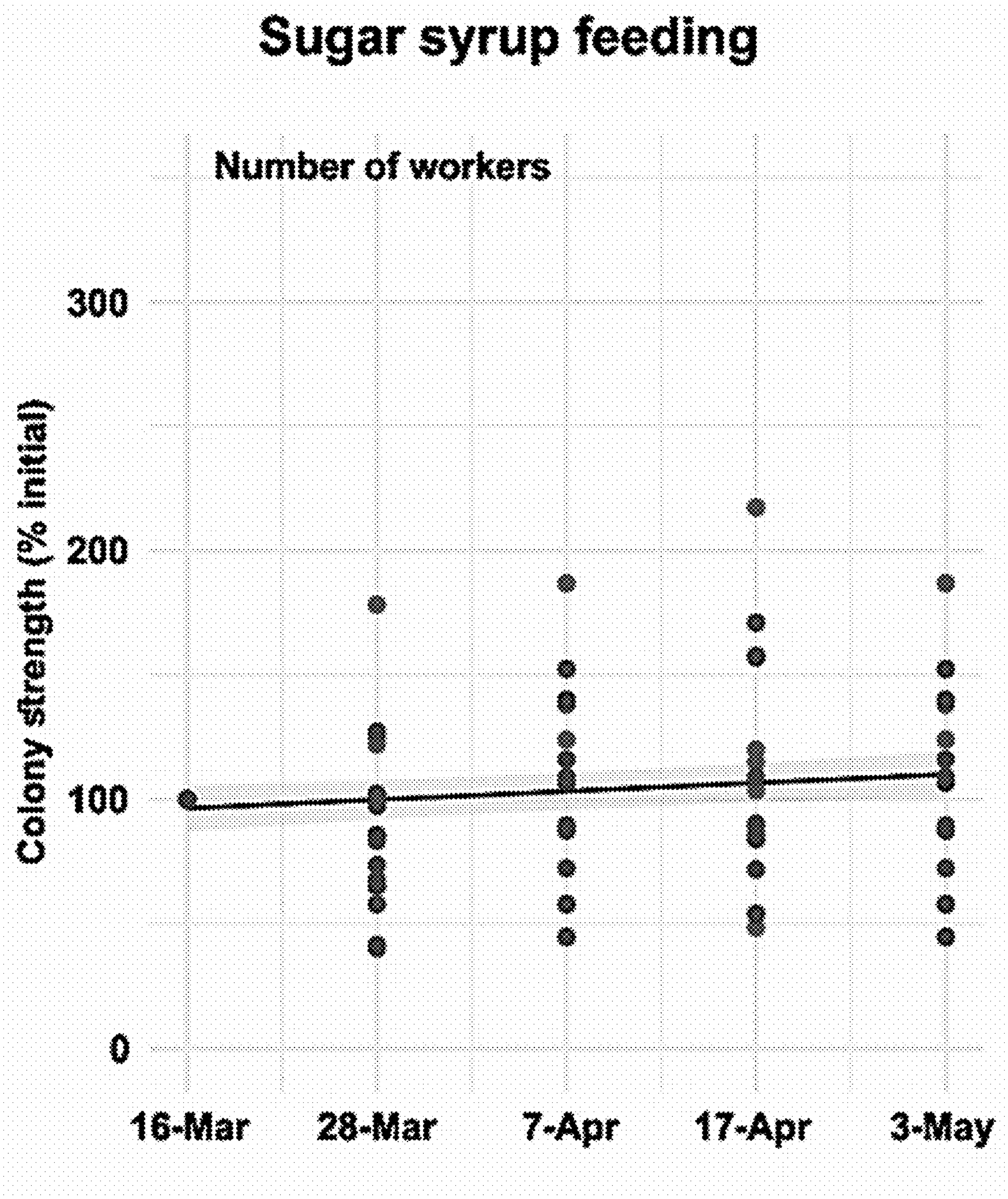
Figure 7A:
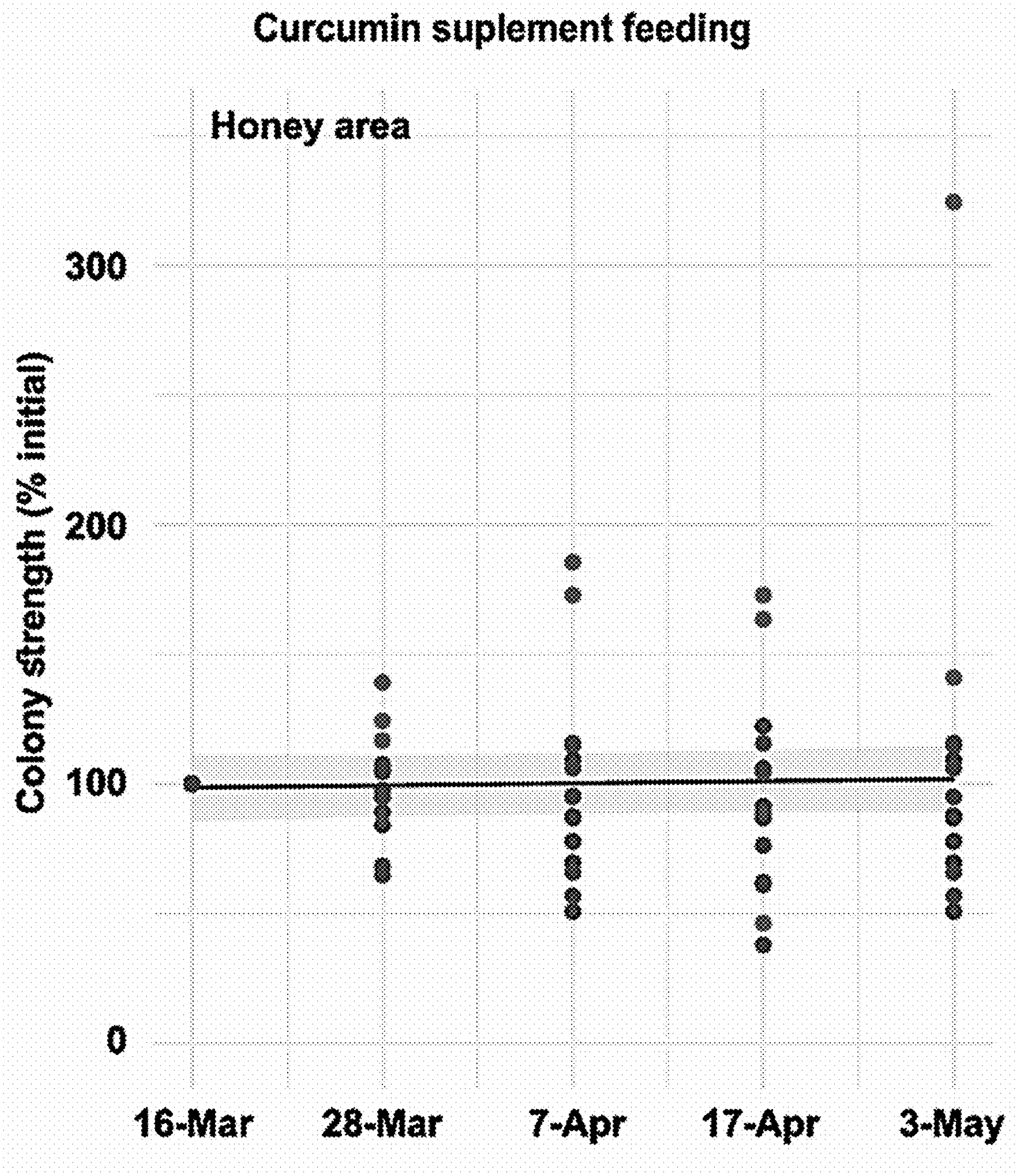
FIGS. 7A to 7D show graphs for explaining the impact of supplement application with 100 ppm of curcumin on the honey area (7A to 7B) and the weight of colony (7C to 7D) in hives given a curcumin-supplemented solution (7A and 7C) and a common sugar solution (7B and 7D)
Figure 7B:
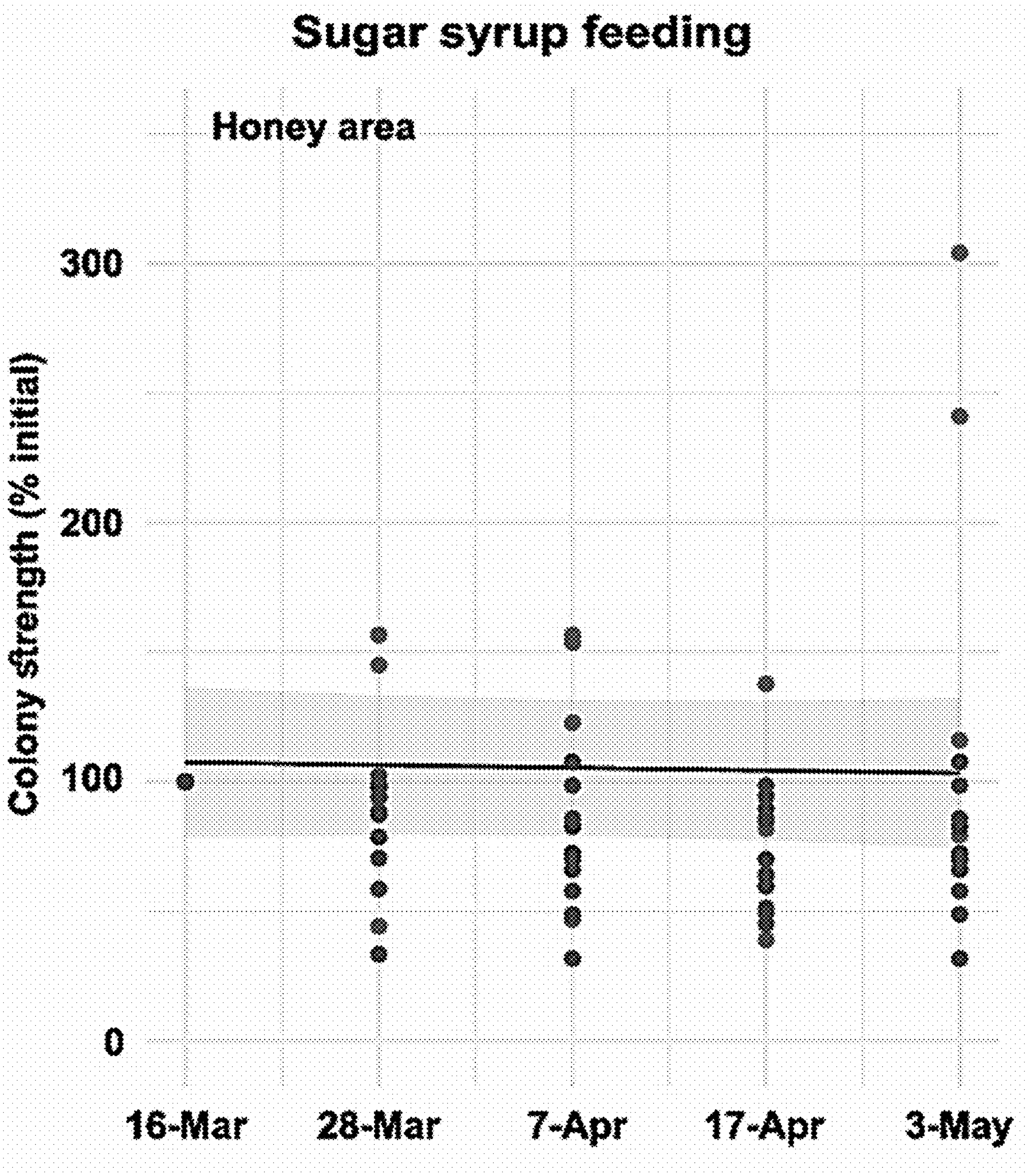
Figure 7C:
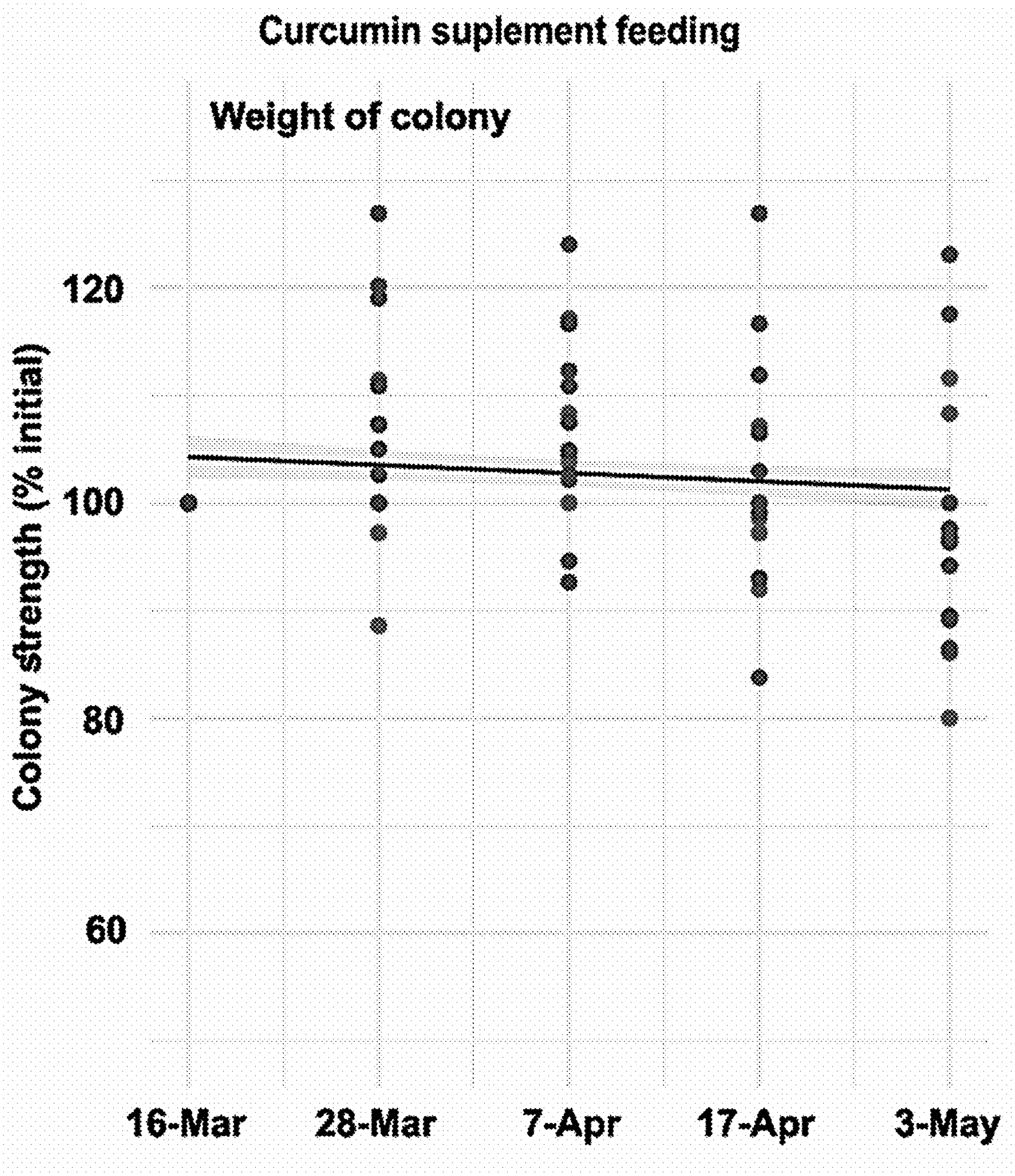
Figure 7D:
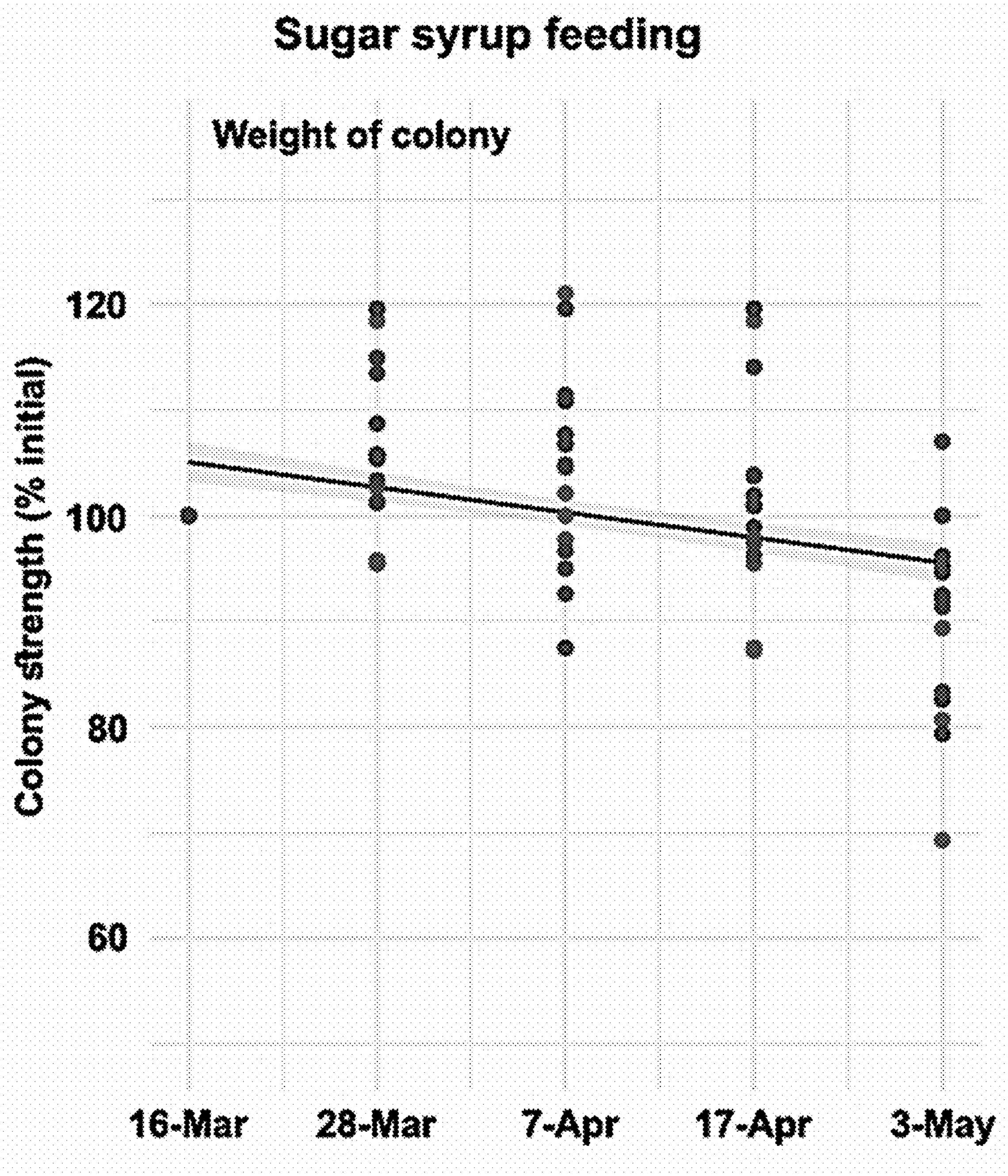
Figure 8:
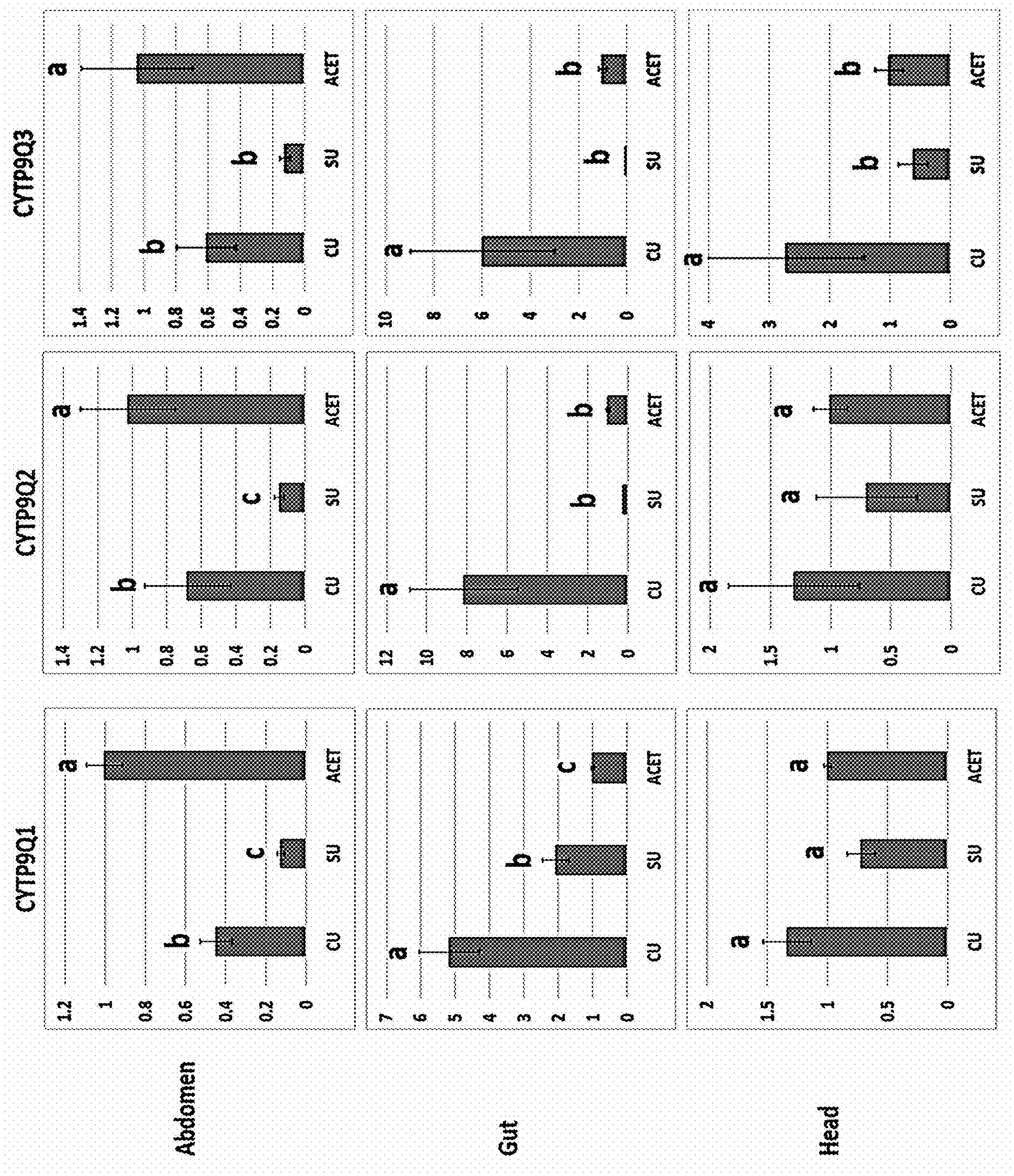
FIGS. 8 and 9 show graphs for explaining gene expression analysis of detoxification enzymes in SU (50% sugar syrup), CU (50% sugar syrup+200 ppm of curcumin), and the control group (ACET, exposed to only 2 ul of acetone and given sugar), 24 hours after being exposed to carbaryl.
Figure 9:
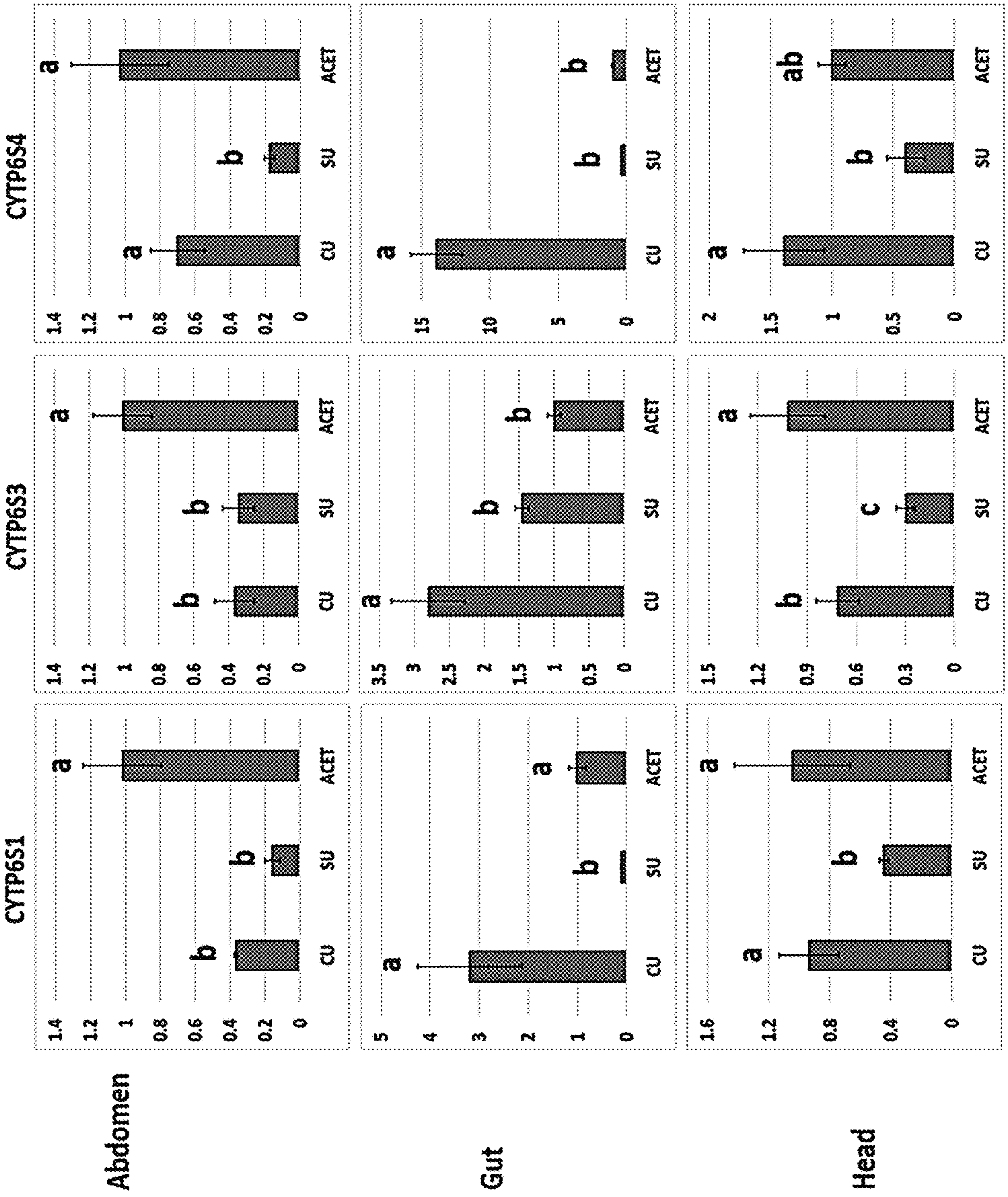

FIG. 1 is a flow chart showing a method of reducing toxicity damage to honeybees from a carbaryl insecticide according to the present disclosure, FIG. 2 is a flow chart showing a method of reducing toxicity damage to different honeybees from a carbaryl insecticide, FIGS. 3A and 3B show graphs for explaining the impact of curcumin application at varying concentrations on the survival of honeybees (3A) and foragers (3B) topically poisoned by carbaryl, FIG. 4 is a graph of a Kaplan-Meier survival curve for test honeybees (*Apis mellifera*) chronically exposed to 2.5 and 5 ppm of carbaryl through oral exposure, FIGS. 5A and 5B show graphs of the mortality rate of honeybees for 10 days after being chronically exposed to 2.5 ppm (5A) and 5 ppm (5B) of carbaryl, FIGS. 6A to 6D show graphs for explaining the impact of supplement application with 100 ppm of curcumin on the honeycomb area (6A to 6B) and the number of workers (6C to 6D) in hives given a solution supplemented with curcumin (100 ppm) (6A and 6C) and a common sugar solution (6B and 6D), FIGS. 7A to 7D show graphs for explaining the impact of supplement application with 100 ppm of curcumin on the honey area (7A to 7B) and the weight of colony (7C to 7D) in hives given a curcumin-supplemented solution (7A and 7C) and a common sugar solution (7B and 7D), and FIGS. 8 and 9 show graphs for explaining gene expression analysis of detoxification enzymes in SU (50% sugar syrup), CU (50% sugar syrup+200 ppm of curcumin), and the control group (ACET, exposed to only 2 ul of acetone and given sugar), 24 hours after being exposed to carbaryl.

A honeybee antidote composition and a method of reducing toxicity damage to honeybees from a carbaryl insecticide will be explained with reference to FIGS. 1 to 9.

The honeybee antidote composition for the carbaryl insecticide contains curcumin capable of increasing the survival rate of honeybees poisoned by the carbaryl insecticide while serving as an effective antidote for insecticide toxicity to honeybees at a concentration in a range of 30 to 300 ppm.

The honeybee antidote composition for the carbaryl insecticide contains curcumin capable of increasing the survival rate of honeybees poisoned by the carbaryl insecticide while serving as an effective antidote for insecticide toxicity to honeybees at the most preferable concentration in the range of 90 to 110 ppm. In this case, curcumin may dramatically increase the activity of oxidases performing a role in detoxification.

An experimental method of the present disclosure, which enables curcumin to increase the survival rate of honeybees poisoned by carbaryl, a carbamate-based insecticide, and to serve as an effective antidote for insecticide toxicity to honeybees, will be described. After screening various substances that are likely to detoxify insecticide toxicity, curcumin is selected.

Adult honeybees are exposed to pesticides through food intake and contact, and whether there is an effect of reducing mortality rate is examined through the consumption of a candidate antidote.

Next, concentrations enabling curcumin to exhibit an effect of selectively detoxifying carbaryl toxicity are examined through concentration treatment.

Through long-term exposure studies, the occurrence of long-term phytotoxicity and an ability to reduce toxicity ability are assessed. With the application of 100 ppm of curcumin under greenhouse conditions, whether the condition of colonies is harmed, and whether toxic substances are removed are assessed.

Next, additional experiments on the activity of detoxification enzymes are performed to examine whether the activity of the detoxification enzymes is high when treated with 100 ppm of curcumin. FIG. 1 is a flow chart showing a method of reducing toxicity damage to honeybees from the carbaryl insecticide according to the present disclosure.

First, a 50% sucrose aqueous solution is prepared (S1).

Next, curcumin is added to the prepared 50% sucrose aqueous solution to a concentration in a range of 30 to 300 ppm (S2).

then, honeybees are fed the 50% sucrose aqueous solution containing curcumin (S3).

FIG. 2 is a flow chart showing a method of reducing toxicity damage to different honeybees from the carbaryl insecticide.

First, a 50% sucrose aqueous solution is prepared (S11).

Next, curcumin is added to the prepared 50% sucrose aqueous solution to a concentration in a range of 90 to 110 ppm (S12).

Then, honeybees are fed the 50% sucrose aqueous solution containing curcumin (S13).

Curcumin was applied at varying concentrations (50, 100, and 200 ppm) to assess the impact thereof on the survival of honeybees intentionally poisoned by carbaryl. These experiments were performed separately on newly emerged honeybees and foragers. While 0.063 ug of an insecticide was administered to the chest of each newly emerged honeybee, 0.11 ug of the insecticide was applied to each forager bee. The intoxicated honeybees were exposed to carbaryl and then fed supplementary food. While the control group consumed only sugar syrup, the experimental group consumed supplementary food containing curcumin. All honeybee groups were fed for 48 hours under controlled laboratory conditions.

The impact observed when adding 100 ppm of curcumin to greenhouses for growing melons was assessed. Thirty greenhouses owned by three farmers were used in this study. While one group of honeybees was given a solution supplemented with 100 ppm of curcumin (CU100), the control hives were given only 50% sugar syrup. Colony strength factors were measured every 10 days.

As a result, it was confirmed through the feeding of the candidate antidote after exposing the adult honeybees (nurse bees and field bees) to pesticides through contact that there was an effect of reducing the mortality rate.

The same results were confirmed through long-term drug contact and antidote administration.

The results of outdoor experiments also showed that the activities of honeybees were excellent in the case of the group treated with 100 ppm of curcumin.

Therefore, it was proven that the concentration of curcumin at 100 ppm had an effect of selectively detoxifying carbaryl toxicity.

Next, as a result of additionally experimenting on the activity of detoxification enzymes and the like, it was confirmed that the activity of the detoxification enzymes was at an even higher level when treated with 200 ppm of curcumin.

In laboratory experiments, the control group administered only sugar syrup had a high mortality rate of 78% out of all the honeybees exposed to carbaryl. A noticeable reduction in the mortality rate of nurse bees was observed after the administration of curcumin at varying concentrations. The significance of such reduction became more evident when higher doses of antidotes corresponding up to 100 ppm were applied to newly emerged honeybees. In experiments performed on foragers after parallel feeding, individuals treated with CU50 and CU100 showed significantly lower mortality rates than those in the control group. According to the analysis herein, it was shown that CU100, when applied after feeding, was enabled to serve as an effective antidote to reduce the side effects of carbaryl on intoxicated honeybees.

In field experiments, the impact of CU100 on the colony strength factor of the colonies used for pollination of Seongju melon was assessed. According to the results, it was observed that while the brood area tended to increase in the group given CU100, the brood area tended to decrease in the control group. Similarly, the number of workers tended to slightly increase in both groups. While the honey area remained consistent throughout the study, a slight increase was observed in hives given CU100, and a slight decrease was observed in hives given only sugar syrup. Despite an overall decrease in colony weight in both groups, the colony given CU100 showed a less steep decrease than the colony given only sugar syrup.

As a result, the curcumin application was involved to relieve the negative impact of pesticides on honeybees. Curcumin was selected due to having well-known biological activities, including anti-inflammatory, antioxidant, and detoxification properties. The present disclosure aimed to assess the impact of curcumin on reducing the mortality rate of honeybees after being exposed to pesticides.

As a result of experiments performed on honeybees exposed to carbaryl (0.063 ug/bee) and later on nurse honeybees fed curcumin at a concentration of 100 ppm, it was shown that the mortality rate was noticeably reduced. While the mortality rate was 78% in the control group, the mortality rate was reduced to 28% in the group given CU100. In the case of foragers, the control group showed a mortality rate of 34%, which dropped significantly to 18% and 16% in the groups given CU50 and CU100 after feeding, respectively.

In field experiments, CU100 was shown to have a positive impact on the colony strength factors of the colonies used for melon pollination, compared to that of the colony fed only sugar syrup. The study results of the present disclosure suggest that curcumin may serve as an effective antidote for insecticide toxicity to honeybees. When adding such a compound to food, the possibility of survival in environments even when exposed to pesticides may greatly increase. Apple pollination service providers are encouraged to contain CU in sugar solutions provided to honeybees. Considering the positive effects of curcumin on colonies associated with pollination of greenhouse melons, it is recommended to contain CU as a supplementary ingredient in a diet.

FIGS. 3A and 3B show graphs for explaining the impact of curcumin application at varying concentrations on the survival of honeybees (3A) and foragers (3B) topically poisoned by carbaryl.

In indoor feeding experiments performed on nurse bees and field bees, 100 ppm of curcumin stably reduced the mortality rate from 80 to 24 and from 35 to 18, respectively. In additional indoor feeding experiments performed on nurse bees and field bees, 50 ppm of curcumin also reduced the mortality rate from 80 to 50 and from 35 to 24, respectively. However, the effect of reducing the mortality rate in this case was not as strong as that in the case of the colony to which 100 ppm of curcumin was applied.

In this case, when looking at the mortality rate when treated with curcumin at concentrations of 90, 100, and 110 ppm in indoor feeding experiments performed on nurse bees and field bees, curcumin application at 90 ppm shows a better effect (80 to 33, and 35 to 24) than curcumin application at 50 ppm. However, the mortality rate increased again with curcumin application at 110 ppm (80 to 34, and 35 to 24).

FIG. 4 is a graph of a Kaplan-Meier survival curve for test honeybees (*Apis mellifera*) chronically exposed to 2.5 and 5 ppm of carbaryl through oral exposure.

The Su group was given only sugar syrup, and the CU group was given 50% sugar syrup and 100 ppm of curcumin.

In long-term indoor feeding experiments, CU (100 ppm of curcumin) treatment did not cause toxicity. Additionally, in exposure experiments to carbaryl, the survival rate of honeybees was highest when treated with 100 ppm of curcumin.

FIGS. 5A and 5B show graphs of the mortality rate of honeybees for 10 days after being chronically exposed to 2.5 ppm (5A) and 5 ppm (5B) of carbaryl.

The control group was administered only sugar syrup, and the CU group was administered 50% sugar syrup and 100 ppm of curcumin.

In long-term exposure experiments to carbaryl, treatment with 100 ppm of curcumin exhibited effects of reducing the mortality rate of honeybees from 38% to 21% and from 78% to 55%.

FIGS. 6A to 6D show graphs for explaining the impact of supplement application with 100 ppm of curcumin on the honeycomb area (6A to 6B) and the number of workers (6C to 6D) in hives given a solution supplemented with curcumin (100 ppm) (6A and 6C) and a common sugar solution (6B and 6D).

In long-term exposure experiments in melon greenhouses at Seongju, while the number of both adult and larval honeybees tended to increase in the group treated with 100 ppm of curcumin, the number of larvae honeybees decreased in the colonies treated with only the sucrose solution.

FIGS. 7A to 7D shows graphs for explaining the impact of supplement application with 100 ppm of curcumin on the honey area (7A to 7B) and the weight of colony (7C to 7D) in hives receiving a curcumin-supplemented solution (7A and 7C) and a common sugar solution (7B and 7D).

In long-term exposure experiments in melon greenhouses at Seongju, there was no change in the weight of honey storage (honey). However, the rate of hive weight reduction was lower in the group treated with 100 ppm of curcumin than in the colonies treated with only the sucrose solution.

FIGS. 8 and 9 show graphs for explaining gene expression analysis of detoxification enzymes in SU (50% sugar syrup), CU (50% sugar syrup+200 ppm of curcumin), and the control group (ACET, exposed to only 2 ul of acetone and given sugar), 24 hours after being exposed to carbaryl.

It is confirmed from FIG. 8 that the activity of oxidases performing a role in the detoxification in the intestine of honeybees dramatically increases in the Cu-treated group compared to that in the untreated group.

The activity in the head of honeybees was shown to be similar to that in the case of the untreated group. Additionally, it is confirmed from FIG. 9 that the activity was extremely low in sites to which the sucrose solution was added after being treated with carbaryl.

According to the honeybee antidote composition and the method of reducing the toxic damage to honeybees from the carbaryl insecticide, curcumin is provided at the most preferable concentration in the range of 90 to 110 ppm and thus is enabled to increase the survival rate of honeybees poisoned by the carbaryl insecticide while serving as an effective antidote for insecticide toxicity to honeybees.

Additionally, curcumin may not only increase the survival rate of honeybees poisoned by the carbaryl insecticide but also perform a better role in the detoxification of honeybees from the insecticide toxicity and dramatically increase the activity of oxidases performing a role in detoxification.

What is claimed is:

1. A method of reducing toxic damage to a honeybee from a carbaryl insecticide, the method comprising:

preparing a 50% sucrose aqueous solution;

adding curcumin to the prepared 50% sucrose aqueous solution to a concentration in a range of 30 to 300 ppm; and feeding a honeybee the 50% sucrose aqueous solution comprising curcumin.

2. The method of claim 1, wherein the adding of curcumin comprises adding curcumin to the 50% sucrose aqueous solution to a concentration in a range of 90 to 110 ppm.

* * * * *